United States Patent [19]
Lee

[11] Patent Number: 5,064,447
[45] Date of Patent: Nov. 12, 1991

[54] PROCESS FOR RECOVERING ORGANIC VAPORS FROM AIR

[75] Inventor: Kung H. Lee, Chadds Ford, Pa.

[73] Assignee: E. I. Du Pont de Nemours and Company, Wilmington, Del.

[21] Appl. No.: 649,351

[22] Filed: Feb. 1, 1991

Related U.S. Application Data

[63] Continuation of Ser. No. 500,258, Mar. 27, 1990, abandoned.

[51] Int. Cl.$^5$ .................. B01D 53/04; B01D 53/22
[52] U.S. Cl. .................................. 55/16; 55/23; 55/62; 55/68; 55/74
[58] Field of Search .................. 55/16, 23, 62, 68, 74, 55/75, 179, 180, 158

[56] References Cited

U.S. PATENT DOCUMENTS

| | | | |
|---|---|---|---|
| 4,104,039 | 8/1978 | Kuri et al. | 55/62 X |
| 4,119,417 | 10/1978 | Heki et al. | 55/16 X |
| 4,140,499 | 2/1979 | Ozaki et al. | 55/16 X |
| 4,289,505 | 9/1981 | Hardison et al. | 55/180 X |
| 4,316,364 | 2/1982 | Spauschus | 62/129 |
| 4,417,451 | 11/1983 | Spauschus | 62/129 |
| 4,421,532 | 12/1983 | Sacchetti et al. | 55/62 X |
| 4,553,983 | 11/1985 | Baker | 55/16 |
| 4,639,257 | 1/1987 | Duckett et al. | 55/16 |
| 4,690,695 | 9/1987 | Doshi | 55/16 |
| 4,701,187 | 10/1987 | Choe et al. | 55/16 |
| 4,738,691 | 4/1988 | Frey | 55/16 X |
| 4,772,295 | 9/1988 | Kato et al. | 55/16 |
| 4,846,852 | 7/1989 | Schweitzer et al. | 55/180 X |
| 4,859,216 | 8/1989 | Fritsch | 55/180 X |
| 4,863,492 | 9/1989 | Doshi et al. | 55/16 |
| 4,906,256 | 3/1990 | Baker et al. | 55/16 |
| 4,915,838 | 4/1990 | Bonne et al. | 55/16 X |
| 4,930,294 | 6/1990 | Meier | 55/180 |
| 4,934,148 | 6/1990 | Prasad et al. | 55/16 X |

FOREIGN PATENT DOCUMENTS

| | | | |
|---|---|---|---|
| 3844326 | 5/1989 | Fed. Rep. of Germany | 55/23 |

OTHER PUBLICATIONS

Daryl L. Roberts & Gordon D. Ching, "Recovery of Freon Gases with Silicone Rubber Membranes", *Ind. Eng. Chem. Process Des. Dev.*, vol. 25, No. 4, 1986, 971-973.

R. W. Baker et al., "Membrane Research in Energy and Solvent Recovery From Industrial Effluent Streams", DOE report, Nov. 1983, pp. 15-24.

*Primary Examiner*—Robert Spitzer
*Attorney, Agent, or Firm*—Robert B. Stevenson

[57] ABSTRACT

A process for separating and recovering organic vapors (e.g., chlorofluorocarbons) from a feed stream of organic vapors and air wherein organic vapors are present in the "window concentration" range being too high for conventional carbon adsorption and too low for efficient compression/condensation recovery. By passing the organic vapor and air feed stream through the feed side of a semipermeable membrane unit, a vapor depleted stream exiting the membrane unit can then be processed by conventional carbon adsorption while a vapor enriched stream from the membrane unit can be processed by conventional compression and condensation.

11 Claims, 1 Drawing Sheet

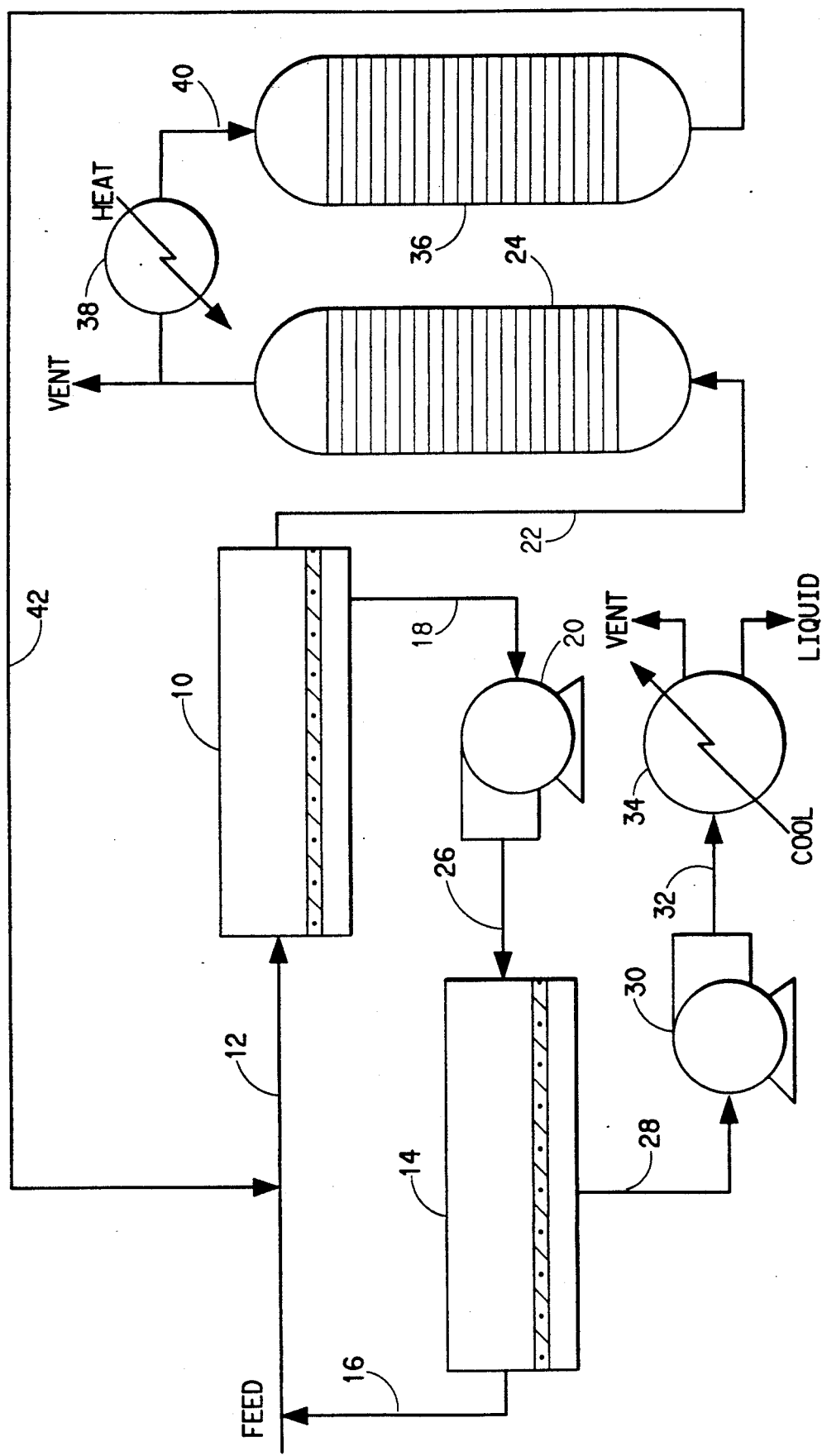
FIGURE

PROCESS FOR RECOVERING ORGANIC VAPORS FROM AIR

This application is a continuation-in-part of application Ser. No. 07/500,258 filed Mar. 27, 1990, now abandoned.

BACKGROUND OF THE INVENTION

1. Field of the Invention

The present invention relates to an improved process for recovering organic vapors from an organic vapor/air mixture wherein organic vapors are present in the so-called "window concentration" range, being too high for conventional carbon adsorption and too low for efficient compression/condensation recovery. More specifically, the present invention relates to separating an organic vapor and air feed stream, by use of a semipermeable membrane unit, into a vapor depleted stream that is then processed by carbon adsorption and a vapor enriched stream that is then processed by compression and condensation.

2. Description of Related Art Including Information Disclosed under §§ 1.97-1.99

It is well known and a common commercial practice to employ organic solvents such as hydrocarbons, halogenated hydrocarbons, oxygenated hydrocarbons and the like in chemical processes, in the production of articles of manufacture, in the cleaning industry as well as in many other applications wherein an organic vapor/air mixture is produced as a by-product or waste stream. Historically such spent organic vapor/air streams would either be vented or flared to the atmosphere. However, contemporary emission standards, stimulated by such considerations as the "greenhouse" effect, potential depletion of stratospheric ozone as well as general health considerations and conservation of resources and basic economic considerations associated with wasting costly raw material, mandate that the organic solvent from the spent vapor/air mixtures be reclaimed.

Generally, the particular solvent and the concentration of its vapor in the air is dependent upon the particular process or application generating the spent stream. When the organic solvent is a high boiling liquid, its recovery can usually be carried out effectively by cooling to condense it to a liquid. However, when the organic solvent is a low boiling liquid there are two traditional methods for its recovery. Thus it is generally known that at high loading of organic vapor in air the organic solvent can be economically reclaimed by compression and condensation and at low loading of organic vapor in the air the organic solvent can be economically reclaimed by carbon adsorption.

The difficulty with the traditional methods is that there is a so-called "window concentration" range (typically from about 6 volume percent to 30 volume percent organic vapor) wherein neither method is practical. At too low of a concentration compression and condensation is inefficient in that greatly increased cost of compression together with reduced amount of solvent recovery and increased emission of uncondensed vapor make the process prohibitively expensive. On the other hand, at too high of a concentration the exotherm associated with carbon adsorption raises the temperature of the adsorbent bed thus reducing the adsorption efficiency and in some cases leading to the possibility of spontaneous combustion. Furthermore, high vapor concentration requires more frequent regeneration of the carbon adsorption tower thus again adding to the cost. At present, if a low boiling organic vapor and air mixture in the "window concentration" range is produced, one must further dilute the stream and then recover the organic phase by adsorption.

In U.S. patent 4,553,983 a process for recovery of organic vapor from a feed stream of air having an organic vapor content of no more than 20,000 ppm by volume (2 volume percent) is disclosed wherein a thin semipermeable membrane with a permeation selectively of at least 50 favoring the organic vapor and a permeability of at least $3 \times 10^{-7}$ cm$^3$(STP).cm/cm$^2$.sec.cmHg is used in combination with a partial vacuum on the permeate side to enrich the permeate with organic vapors. Similarly, in an article by D. L. Roberts et al. entitled "Recovery of Freon Gases with Silicone Rubber Membrane", *Ing. Eng. Chem. Process Design Dev.*, 1986, 25, pp 971-973, the recovery of fluorocarbons and chlorofluorocarbons from air mixtures using a semipermeable membrane is disclosed. In U.S. patents 4,316,364 and 4,417,451 a refrigerant monitor system employing a membrane with a permeation selectivity favoring air relative to the refrigerant is disclosed.

SUMMARY OF THE INVENTION

The present invention provides an improved process for recovering organic vapors from organic vapor/air mixtures, particularly mixtures wherein the concentration of the organic vapor to be recovered is in the so-called "window concentration" range (i.e., too high for efficient recovery by the carbon adsorption method and too low for efficient recovery by the compression/condensation method). The improved method according to the present invention involves the simultaneous use of a membrane separation system in combination with a conventional carbon adsorption system and a conventional compression/condensation system, thus producing a hybrid recovery unit. According to one embodiment of the present invention, a two-stage membrane separation system is used to produce a feed side effluent at the first stage that is sufficiently depleted of organic vapors that it can be treated by conventional carbon adsorption. The permeate from the first stage is then introduced to the feed side of the second stage of the membrane separation system to produce further organic vapor enriching of the second stage permeate that is then treated by conventional compression and condensation. The feed side effluent of the second stage is recycled to the feed side of the first stage. Such a process is particularly useful in recovering chlorofluorocarbon, hydrochlorofluorocarbon, and hydrofluorocarbon vapors emitted to the air during the manufacture of various foamed plastic products and the like. In another embodiment of the present invention, a feed side effluent at the first stage of a two-stage membrane separation system is organic vapor enriched and sent to the compression/condensation separator while the permeate from the second stage is organic vapor depleted and, therefore, processed by carbon adsorption. Further according to the present invention, a regeneration/recycle procedure employing multiple carbon adsorption beds and the return of effluent from an adsorption bed being regenerated with an in situ stream is provided to further reduce emission of the halocarbon.

Thus, the present invention provides a process for separating and recovering organic vapors from a feed stream of organic vapor and air wherein organic vapors are present in the "window concentration" range, being too high for conventional carbon adsorption and too low for efficient compression/condensation recovery, comprising the steps of:

(a) providing a semipermeable membrane means for separating organic vapors from air having a feed side and a permeate side wherein said semipermeable membrane means is characterized as having a selectivity for allowing the passage of organic vapor relative to air or for allowing the passage of air relative to organic vapor of at least 10 and permeability for the permeate gas of greater than $1 \times 10^{-7}$ cm$^3$(STP).cm.cm$^{-2}$.cmHg$^{-1}$.sec$^{-1}$;

(b) passing a feed stream of organic vapor and air, wherein said organic vapor is present in the "window concentration" range, across the feed side of the semipermeable membrane such that organic vapor or air, but not both, passes preferentially through the membrane to form an organic vapor depleted air stream characterized by an organic vapor concentration below the "window concentration" range and an organic vapor enriched stream characterized by an organic vapor concentration above the "window concentration" range;

(c) subjecting said organic vapor depleted air stream produced in step (b) to carbon adsorption, thus separating and recovering organic vapor therefrom; and (d) subjecting said enriched stream produced in step (b) to compression and condensation, thus separating and recovering organic vapor therefrom.

It is an object of the present invention to provide an improved process for the efficient and economic recovery of low boiling organic solvent vapors from an organic vapor and air mixture, wherein the organic vapor to air mixture is at a concentration such that the organic vapor concentration is too low for efficient recovery by compression/condensation methods and too high for efficient recovery by carbon adsorption methods. It is an additional object of the present invention to provide an efficient method of recovering low boiling organic solvent vapors from the above-described vapor/air mixtures by use of a semipermeable membrane separation stage that works in combination, simultaneously, with a conventional carbon adsorption system and a conventional compression/condensation system. It is still a further object of the present invention to provide a hybrid membrane-carbon-adsorption-compression/-condensation vapor recovery system that will recover chlorofluorocarbons from a chlorofluorocarbon and air mixture particularly those associated with the commercial use of blowing and foaming agents in the manufacture of foamed plastics, fibers, films and the like. Fulfillment of these objects and the presence and fulfillment of other objects will be apparent upon complete reading of the specification and claims taken in conjunction with the attached drawing.

BRIEF DESCRIPTION OF THE DRAWING

The Figure represents a schematic illustration of a typical improved process for recovery of organic vapors according to one embodiment of the present invention.

DESCRIPTION OF THE PREFERRED EMBODIMENTS

The improved process for recovering organic vapors from an organic vapor/air mixture according to the present invention, how it differs from yet is related to previously known methods of recovering organic vapors, what advantages there are associated with the use of the improved method relative to these prior art methods, and under what circumstances the present invention provides these advantages can be best explained and understood by reference to the drawing.

The schematic flow diagram of the Figure illustrates the basic components and stages of one particular embodiment of the present invention. As illustrated in the Figure, a feed stream (i.e., a halocarbon/air mixture in the "window concentration" range) is continuously introduced into the first stage 10 of the two-stage semipermeable membrane units via line 12. This gaseous feed stream entering the feed side of first stage membrane separator 10 is continuously commingled with the recycle gaseous effluent from the feed side of the second membrane separator 14, via line 16, prior to the combined mixture being sent to membrane separator 10. Within separator 10 (in this particular illustrated embodiment) an organic vapor enriched permeate is continuously withdrawn via line 18 by virtue of vacuum blower 20 while an organic vapor depleted stream is withdrawn from the feed side via line 22 and sent to (again in this particular illustrated embodiment) one of two essentially equivalent carbon absorber units, 24, for recovery of the organic vapors. The permeate from the first stage membrane separator 10 is then delivered to the feed side of the second stage separator 14 via line 26. Within separator 14 further organic vapor enriching of the permeate occurs with the permeate being withdrawn via line 28 by virtue of vacuum blower/compressor 30 and sent, via line 32, to condenser/separator 34. The effluent from the feed side of membrane separator 14, having an organic vapor concentration substantially the same as the original feed, is continuously returned and commingled with the feed as previously mentioned.

During operation of the embodiment of the Figure, liquid halocarbon is continuously removed from the bottom of the condenser/separator 34 while halocarbon is simultaneously being deposited on the carbon bed within absorber 24. Halocarbon depleted air may be vented from both the absorber 24 and condenser/-separator 34. Because of the finite capacity of the carbon adsorption bed, an additional adsorption unit 36 is provided for continuous operation. While bed 24 is actively adsorbing halocarbon the other adsorption unit 36 can be regenerating. The Figure illustrates regeneration in that a portion of the air effluent from absorber 24 is passed through heater 38 and introduced into absorber 36 via line 40. The halocarbon thus removed from the regenerating absorber 36 is then sent back to an appropriate location in the overall process for further isolation and recovery of halocarbon. As illustrated in the Figure the recycle of halocarbon enriched regeneration gas is being directed via line 42 to the feed stream entering the first membrane separation unit 10. It should be appreciated that depending on the level or concentration of halocarbon in this recycle loop, the regeneration stream can be reintroduced advantageously to other locations in the overall process, including the permeate side of the first membrane unit 10 or even directly to the compression/condensation unit if the halocarbon concentration is sufficiently high. It should also be appreciated that various additional valves, conduits, and heat exchangers and the like (not shown in the Figure) can be incorporated into the process, as generally known in the art, to accomplish the switching of absorber units and regeneration with recycle features of the present invention.

It should be appreciated that the particular two-stage embodiment illustrated in the Figure is most useful when the feed stream is relatively dilute with respect to the so-called "window concentration" range or, stated in other terms, when the feed stream is sufficiently dilute to be further depleted of organic vapors in a single membrane stage such as to be amenable to carbon adsorption. Thus, in principle, the process according to the present invention is contemplated as being useful in embodiments that involve a single stage membrane unit, a series or sequence of membrane units wherein the final pair of stages involve a recycle loop. The basic point of interest in each of these embodiments is that the use of the semipermeable membrane unit, although not achieving isolation and recovery of the organic vapor per se, does produce simultaneously an organic vapor enriched and an organic vapor depleted gaseous stream without external dilution which can then be further treated by conventional carbon adsorption and compression/condensation to recover the organic phase. It should be further appreciated that the specific embodiment illustrated in the Figure is to be employed with a semipermeable membrane that is selective with respect to the preferential passage of organic vapor relative to air. When a semipermeable membrane selective to the passage of air relative to organic vapor is employed, the role of the carbon adsorption unit 24 and the compression/condensation unit, 30 and 34, are interchanged.

The advantages of the improved process for recovering organic solvent vapors according to the present invention are significant and numerous. First and foremost, the improved method affords an efficient and technically convenient method of recovering solvent vapors from feed streams that are in the "window concentration" range, without resorting to excessive dilution, oversized adsorption towers, frequent regeneration of columns or taxing the capacity of existing adsorption tower to its limit or, alternatively, forcing the compression/condensation equipment to operate under impractical and inefficient conditions including possible excessive emission losses. By eliminating the need for further dilution yet producing a vapor depleted effluent stream for conventional carbon adsorption, the overall capacity of a given adsorption tower is optimized and the risks associated with relatively high concentration of vapors (excessive exotherms, hot spots and/or spontaneous combustion) is significantly reduced. Simultaneously, the production of an effluent stream enriched in organic vapors further optimizes the compression/condensation step used to isolate and recover the organic solvent.

The particular feed streams that are amenable to the aforementioned advantages and benefits of the present invention are generally any low-boiling organic solvent vapor mixed with air or similar carrier gas wherein the concentration of the organic vapor phase is within the "window concentration" range. For purposes of this invention, the organic vapor would include, by way of example, but not limited thereto, low-boiling hydrocarbons, halogenated hydrocarbons, oxygenated hydrocarbons and the like. The present invention is viewed as being particularly useful in the recovery of halogenated hydrocarbons frequently employed in commercial cleaning processes and as solvent or blowing/foaming agents in many plastic fabrication and article manufacturing processes. In particular, this would include the chloro- and/or fluorocarbons, the chlorofluorocarbons and the hydrochlorofluorocarbons as commonly known and used in industry.

Generally when the organic solvent is a liquid with relatively high boiling point, its recovery is relatively simple (i.e., cooling to bring about condensation provides efficient recovery). In contrast, when the organic solvent is a liquid with relatively low boiling point, such as a boiling point below about 40° C. wherein a large portion of the solvent is in the vapor state at ordinary temperatures, simple condensation is not sufficient. Currently, there are two traditional methods available for vapor recovery for low boiling organic solvents, i.e., either by compression/condensation or by use of an adsorbent. Unfortunately, for many organic vapor/air mixtures there is an upper limit to that concentration of organic vapors that can be processed by say carbon adsorption and a minimum concentration required to efficiently recover vapor by compression/condensation. In such cases a "window concentration" range may exist wherein the concentration of organic vapor present in the air or carrier gas is too high for conventional carbon adsorption and too low for efficient compression/condensation recovery. It should be appreciated that the specific concentration associated with this so-called "window concentration" range may vary according to the specific organic vapor and the carrier gas as well as the operating conditions being employed. Thus, generally and for purposes of this invention, the "window concentration" range can be defined by viewing or considering what concentration cannot be efficiently processed by conventional means.

However, as an alternative to this definition, the "window concentration" range can be interpreted from an affirmative viewpoint by considering the concentration ranges that can be advantageously processed by the improved process according to the present invention. To a great extent these viewpoints are synonymous but the latter definition may tend to broaden the specific quantitative concentration range.

Thus, for example, when the concentrations of solvent vapor are sufficiently high in solvent/air mixture, say about 30 volume percent, efficient recovery is possible by the compression/condensation method wherein the solvent/air mixture is compressed and cooled to condense the solvent vapor into liquid solvent. The liquefied solvent can then be separated and stored for further use. When the concentration of solvent vapor in solvent/air mixture is low, for example about 6 volume percent or lower, efficient recovery is possible by the carbon adsorption method wherein such solvent air mixture is contacted with activated carbon. Typically this is performed in an adsorption tower, wherein the solvent is preferentially adsorbed on the carbon and air devoid of solvent can be released into the atmosphere. When the carbon in the adsorption tower is saturated with the solvent, the solvent/air stream is directed to another adsorption tower. Solvent adsorbed on carbon can then be recovered by a number of ways such as by raising the temperature or passing steam through the tower.

However, when the concentration of low boiling solvent in a solvent/air mixture is between from about 6 volume percent and about 30 volume percent, the above-described solvent recovery processes become inefficient and uneconomical. The present invention provides an improvement in solvent recovery process wherein low boiling solvent in a solvent/air mixture is present in a concentration range which makes recovery by either compression/condensation or carbon adsorption method impractical and uneconomical. In principle, the present invention provides a process for treating a solvent/air mixture in the above-described "window concentration" range to obtain two different solvent/air mixtures; i.e., one in which the solvent concentration is sufficiently high for efficient recovery by the compression/condensation method and the other in which the concentration of the solvent is sufficiently low for efficient recovery by the carbon adsorption method.

The semipermeable membrane unit useful in the present invention can be generally any such device as well known in the art, including by way of example, but not limited thereto, semipermeable membrane thin layer of film, spiral wound membrane, hollow fiber semipermeable membrane or the like. For the semipermeable membrane to separate the organic vapor/air mixture into a vapor enriched component and a vapor depleted component, there must be a difference in the permeation rates for the organic vapor and air (i.e., $O_2$ and $N_2$). For purposes of this invention the ratio of permeation rate for the organic vapor through the barrier membrane to the permeation rate for air (usually measured with respect to nitrogen) should be at least 10. Preferably this selectivity (or separation factor) should be 100 or even up to 10,000 with the actual absolute permeation rate of organic vapor being typically at least $1 \times 10^{-7}$ $cm^3(STP).cm.cm^{-2}.cmHg^{-1}.sec^{-1}$ or greater. Typically, the barrier membrane is an elastomeric polymer film made from natural rubbers, polyiosprenes, polybutenes, polybutadienes, silicone rubbers, neoprene or the like as generally known in the art. Preferably, for the separation of chlorofluorocarbons and hydrochlorofluorocarbons from air, wherein the permeation selectivity is to favor passage of the halocarbon, a barrier membrane of dimethyl silicone rubber is employed. When the permeation selectivity is to favor the passage of air, potential barrier membrane materials include glasses, ceramics, polymeric plastics, films and elastomers, natural products such as cellulose and rubber as well as porous metals or metal films, such as stainless steel, palladium, platinum and cold rolled steel, as generally known in the art.

The organic vapor depleted effluent stream from the feed side of the membrane separation unit can be processed for recovery of organic solvent by any of the adsorption tower techniques as generally known in the art. Preferably a carbon adsorption is used, but for purposes of this invention other conventional adsorption units based on molecular sieve or adsorption media should be considered equivalent to the preferred carbon adsorption. Typically such systems involve a plurality of individual adsorption towers wherein one unit is selectively adsorbing organic vapor as the effluent stream from the membrane section passes through while the other units are being stripped of the organic solvent and regenerated for further vapor adsorption, again as generally known in the art.

The organic vapor enriched permeate stream from the membrane separation unit can be processed by any of the conventional compression and condensation techniques as generally known in the art. Typically the process involves a compression followed by a condenser/heat exchange which is adapted to recover liquid condensate. The liquid phase organic solvent recovered as well as that recovered from the carbon adsorption process can either be sent to storage or recycled to the particular manufacturing or process system that generated the organic vapor/air mixture being processed.

An example of a process which produces organic vapor/air mixtures wherein the concentration of the organic solvent in the vapor/air mixture is from about 10 to 25 volume percent, i.e., in the "window concentration" range, is in the manufacturing of continuous-fiber, spunbonded polyethylene fabric sheets which are used, for example, in the housing industry. In this flash-extrusion process a chlorofluroocarbon namely, monofluorotrichloromethane ($CFCl_3$, CFC-11; b.p. 23.8° C.) is used as the processing solvent. This solvent is particularly useful because it provides certain processing advantages which lead to superior properties in the finished product. However, this solvent is comparatively expensive and is considered to be a contributor to the stratospheric ozone layer depletion process. Thus, there is a two fold incentive (environmental and economic) to recover as much of this solvent as possible and in a cost effective way.

In this process, polyethylene is intimately mixed and heated with monofluorotrichloromethane in a mixing tank to form a solution of polyethylene in CFC-11. This solution is flash-extruded onto a moving continuous belt in a chamber whereby the CFC-11 is rapidly vaporized. The continuos-fiber polyethylene mat is then bonded by heat and calender pressure to provide the desired spunbonded sheet. The vaporized CFC-11, now admixed with air present in the chamber, has a concentration in the range of from about 10 volume percent to about 25 volume percent. Since this concentration of CFC-11 in the CFC-11/air mixture is too low for efficient recovery by the compression/condensation method and too high for efficient recovery by the carbon adsorption method, it was necessary to add additional air to this mixture such that the concentration of CFC-11 was reduced to below 7 volume percent so that recovery can be made by the carbon adsorption method. The step of adding additional air so the solvent recovery by carbon adsorption method can be used provided problems such as (1) considerably greater volume of solvent/air mixture must now be treated; (2) if lesser amount of air is used to reduce problem (1) above, the efficiency of the adsorption tower is reduced due to temperature rise in the adsorption tower from the heat of adsorption, and, in fact, in some situations, temperature may rise so high that fire may occur in the tower; and (3) since all of the solvent is recovered via the carbon adsorption tower, there is a constant need to switch adsorption towers when it is saturated with CFC-11, and with the attendant need to desorb CFC-11 from carbon and regeneration of the carbon adsorbent, certain loss of CFC-11 into the atmosphere was unavoidable. By the use of the present invention process, there is almost complete recovery of CFC-11 for reuse and the atmospheric release of CFC-11 has been greatly reduced.

The following examples are presented to further illustrate specific embodiments of the invention. In presenting these examples all references to percentages of components in the gaseous phase are by volume percent unless otherwise indicated.

EXAMPLE 1

The improved method according to the present invention was carried out during a commercial process for making polyethylene sheets wherein the process comprised the steps of intimately mixing polyethylene beads with a chlorofluorocarbon (CFC-11), heating and mixing the mixture under pressure and then flash-extruding the solution of polyethylene in CFC-11 onto a continuous moving belt in a chamber at atmospheric pressure containing air. Under these conditions CFC-11 which boils at 23.8° C. vaporizes very rapidly leaving the desired polyethylene sheet on the moving belt. The CFC-11/air mixture exiting the chamber measured during the 51 runs carried out averaged 17.9 volume percent (range of from 10 volume percent to 29 volume percent). Previously this CFC-11/air mixture was diluted with additional air so that CFC concentration was reduced to a few volume percent so that CFC-11 could be recovered by the carbon adsorption method. In carrying out the process of the invention, the CFC-11/air mixture was contacted with semipermeable membrane unit. The semipermeable membrane utilized was an elastomeric dimethyl silicone wherein the membrane is incorporated into spiral wound membrane module. The unit is operated by maintaining the vapor pressure on the permeate side lower than the vapor pressure on the feed side. This is done by operating a vacuum pump on the permeate side. In the 51 runs, the feed to the permeation unit which averaged 17.9 volume percent of CFC-11 was separated into CFC-11 enriched component which averaged 73.82 volume percent CFC-11 (range of 50 volume percent to approaching 100 volume percent) and CFC-11 depleted component which averaged a 6.8 volume percent CFC-11 (range of 3.3 volume percent to 12.0 volume percent). With the average concentration of CFC-11 of 73.8 volume percent which on the average represents enrichment of 4.1 fold, CFC-11 from such a mixture was recovered efficiently by the usual compression/condensation method. The CFC-11 depleted component with an average concentration of CFC-11 of 6.8 volume percent was readily treated in the carbon adsorption tower.

EXAMPLE 2

A continuous feed stream of CFC-11 and air withdrawn from a chamber containing a moving belt upon which a spunbonded, random weave, polyethylene fabric, is being continuously manufactured is fed to a hybrid membrane-carbon-adsorption-compression/condensation system as illustrated in the Figure. This feed stream is delivered at a rate of 1000 scfm and contains an average of 12 volume percent CFC-11. Prior to introduction of the feed stream to the first stage spiral wound membrane unit having a silicon polymer semipermeable membrane, it is combined with a 12 volume percent CFC-11 recycle effluent at a rate of 71.3 scfm from the feed side of the second stage membrane unit. A vacuum blower delivers a 60 volume percent CFC-11 permeate stream from the first stage membrane unit to the second stage membrane unit at a flow rate of 169.1 scfm. The second stage silicone polymer spiral wound membrane unit is used in combination with a second vacuum blower to withdraw a 95 volume percent CFC-11 permeate stream at 97.8 scfm, while the previously mentioned 71.3 scfm, 12 volume percent CFC-11 feed side effluent is recycled to the inlet of the first membrane separator. The 95 volume percent CFC-11 permeate stream at 97.8 scfm is directed to a conventional compressor/condenser stage for final removal and recovery of CFC-11 while a 3 volume percent CFC-11 effluent stream from the feed side of the first membrane separator at a rate of 902.2 scfm is directed to a conventional carbon adsorption unit for separation and recovery of CFC-11.

Having thus described and exemplified the invention with a certain degree of particularity, it should be appreciated that the following claims are not to be so limited but are to be afforded a scope commensurate with the wording of each element of the claim and equivalents thereof.

I claim:

1. A process for separating and recovering organic vapors from a feedstream of organic vapor and air wherein organic vapors are present in the "window concentration" range, being too high for conventional carbon adsorption an tool low for efficeint compression/condensation recovery, comprising the steps of:
   (a) providing a semipermeable membrane means for separating organic vapors rom air having a feed side and a permeate side wherein said semipermeable membrane means is characterized as having a selectivity for allowing the passage of organic vapor relative to air or for allowing the passage of air relative to organic vapor of at least 10 and permeablility for the permeate gas of greater than $1 \times 10^{-7}$ cm$^3$(STP).cm.cm$^{-2}$.cmHg$^{-1}$.sec$^{-1}$;
   (b) passing a feed stream of organic vapor and air, wherein said organic vapor is present in the "window concentration " range of about 6 volume percent to about 30 volume percent organic vapor, across the feed side of the semipermeable membrane such that organic vapor or air, but not both, passes preferentially through the membrane to form an organic vapor depleted air stream characterized by an organic vapor concentration below the "window concentration" range and an organic vapor enriched stream characterized by an organic vapor concentration above the "window concentration " range;
   (c) subjecting said organic vapor depleted air stream produced in step (b) to carbon adsorption, thus separating and recovering organic vapor therefrom; and
   (d) subjecting said enriched stream produced in step (b) to compression and condensation, thus separating and recovering organic vapor therefrom.

2. A process of claim 1 wherein said semipermeable membrane means further comprises a first and second separate semipermeable membrane stage wherein each stage has a feed side and a permeate side and a separate vacuum is provided on the permeate side of each of said stages and wherein said feed stream of organic vapor and air enters the feed side of said first semipermeable membrane stage, the stream exiting the feed side of said first semipermeable membrane stage is subjected to the carbon adsorption or to the compression and condensation, the permeate from said first semipermeable membrane stage is direct to and enters the feed side of said second semipermeable membrane stage, the organic vapor and air stream exiting the feed side of said second semipermeable membrane stage is recycled to said feed stream entering the feed side of said first semipermeable membrane stage, and the permeate from said second semipermeable membrane stage is subjected to the compression and condensation or to the carbon adsorption.

3. A process of claim 2 wherein the semipermeable membrane means allow for the selective passage of organic vapor relative to air and wherein the organic vapor depleted air stream exiting the feed side of said first semipermeable membrane stage is characterized by an organic vapor concentration below the "window concentration " range and is subjected to the carbon adsorption and the organic vapor enriched permeate from said second semipermeable membrane stage is characterized by an organic vapor concentration above the "window concentration " range and is subjected to compression and condensation.

4. A process of claim 3 wherein said organic vapor and air feed stream comprises a halocarbon.

5. A process of claim 2 wherein the semipermeable membrane means allow for the selective passage of air relative to organic vapor and wherein the organic vapor enriched stream exiting the feed side of said first semipermeable membrane stage is characterized by an organic vapor concentration above the "window concentration" range and is subjected to compression and condentiom and the organic vapor depleted permeate from said second semipermeable membrane stage is characterized by an organic vapor concentration below the "window concentration " range and is subjected to the carbon adsorption.

6. A process of claim 2 wherein said organic vapor and air feed stream comprises a halocarbon.

7. A process of claim 2 wherein the subjecting of said organic vapor depleted air stream to carbon adsorption is accomplished by use of at least two carbon adsorption units wherein while one of said carbon adsorption units is being epoyed to adsorb organic vapors at least one other carbon adsorption unit is being regenerated by the steps comprising:
(a) directing at least a portion of the effluent from the carbon adsorption unit adsorbing organic vapors through said other carbon adsorption unit being regenerated at a temperature sufficiently high to remove adsorbed organic vapors from said other carbon adsorption unit; and
(b) recycling the effluent from said other carbon adsorption unit during regeneration to either the feed or permeate side of a semipermeable membrane stage for further separation and recovery of organic vapor.

8. A process of claim 1 wherein the semipermeable membrane means allows of the selective passage of organic vapor relative to air and wherein the organic vapor depleted air stream exiting the feed side of said semipermeable membrane means is characterized by an organic vapor concentration below the "window concentration" range and is subjected to the carbon adsorption and the organic vapor enriched permeate from said semipermeable membrane means is characterized by an organic vapor concentration above the "window concentration" range and is subjected to compression and condensation.

9. A process of claim 1 wherein the semipermeable membrane means allows for the selective passage of air relative to organic vapor and wherein the organic vapor enriched scream exiting the feed side of said semipermeable membrane means is characterized by an organic vapor concentration above the "window concentration " range and is subjected to compression and condensation and the organic vapor depleted permeate from said semipermeable membrane means is characterized by an organic vapor concentration below the "window concentration " range and is subjected to the carbon adsorption.

10. A process of claim 1 wherein said organic vapor and air feed stream comprises a halocarbon.

11. A process of claim 1 wherein the subjecting of said organic vapor depleted air stream to carbon adsorption is accomplished by use of at least two carbon adsorption units wherein while one of said carbon adsorption units is being employed to adsorb organic vapors at least one other carbon adsorption unit is being regenerated by the steps comprising:
(a) directing at least a portion of the effluent from the carbon adsorption unit adsorbing organic vapors through said other carbon adsorption unit being regenerated at a temperature sufficiently high to remove adsorbed organic vapors from said other carbon adsorption unit; and
(d) recycling the effluent from said other carbon adsorption unit during regeneration to either the feed or permeate side of the semipermeable membrane means for further separation and recovery of organic vapor.

* * * * *